(12) United States Patent
Bobrowski

(10) Patent No.: US 8,182,847 B1
(45) Date of Patent: May 22, 2012

(54) METHODS AND COMPOSITIONS TO ENHANCE ENDOGENOUS IGF PRODUCTION AND THEIR USES

(76) Inventor: Paul Bobrowski, Raleigh, NC (US)

( * ) Notice: Subject to any disclaimer, the term of this patent is extended or adjusted under 35 U.S.C. 154(b) by 33 days.

(21) Appl. No.: 12/687,689

(22) Filed: Jan. 14, 2010

Related U.S. Application Data

(63) Continuation of application No. 10/596,655, filed as application No. PCT/US2004/043760 on Dec. 22, 2004, now abandoned, and a continuation-in-part of application No. 10/676,459, filed on Sep. 30, 2003, now abandoned, which is a continuation-in-part of application No. 09/655,598, filed on Sep. 5, 2000, now abandoned.

(60) Provisional application No. 60/531,266, filed on Dec. 22, 2003, provisional application No. 60/152,468, filed on Sep. 3, 1999.

(51) Int. Cl.
*A61K 36/31* (2006.01)
(52) U.S. Cl. .................. 424/755; 424/773; 424/779
(58) Field of Classification Search .................. None
See application file for complete search history.

(56) References Cited

U.S. PATENT DOCUMENTS
6,267,995 B1    7/2001    Zheng et al.

FOREIGN PATENT DOCUMENTS
CN    1080185 A    *    1/1994
JP    2003-238432 A    *    8/2003

OTHER PUBLICATIONS

Haraguchi (Am J Respir Crit Care Med (1999), vol. 159, pp. 1005-1013).*
http://www.hgh-pro.com/hormones.html—accessed Jan. 2012.*
Composition of the essential oil of *Lepidium meyenii* (Walp.), M.R. Tellez et al., Phytochemistry 61 (2002), 149-155.
Axtell ("Minor Oil Crops; Part III: Minor essential oil crops—section II: Distillation of essential oils" (1992) FAO Agricultural Services Bulletin, No. 94).
Hexanic Maca extract improves rat sexual performance more effectively than methanolic and chloroformic Maca extracts, A.F.G. Cicero et al., Andrologia 34, 177-179 (2002).
Effect of *Lepidium meyenii* (MACA) on sexual desire and its absent relationship with serum testosterone levels in adult healthy men, G. F. Gonzales et al., Andrologia 34,367-372 (2002).
Chemical Profiling and Standardization of *Lepidium meyenii* (Maca) by Reversed Phase High Performance Liquid Chromatography, Markus Ganzera, et al., Chem. Pharm. Bull. 50(7) 988-991 (2002).
Effect of *Lepidium meyenii* (Maca), a root with aphrodisiac and fertility-enhancing properties, on serum reproductive hormone levels in adult healthy men, G F Gonzales et al., Journal of Endocrinology (2003) 176,163-168.
*Lepidium meyenii* Walp. improves sexual behaviour in male rats independently from its action on spontaneous locomotor activity, A.F.G. Cicero, Journal of Ethnopharmacology 75 (2001) 225-229.
Constituents of *Lepidium meyenii* 'maca', Ilias Muhammada et al., Phytochemistry 59 (2002) 105-110.

* cited by examiner

*Primary Examiner* — Susan Hoffman
(74) *Attorney, Agent, or Firm* — Venable Campillo Logan & Meaney P.C.

(57) ABSTRACT

An extract and procedure for extracting the polar constituents from plants of the Family Brassicaceae, specifically but not limited to the genus *Lepidium*. The extract has increased polar and decreased lipidic constituent concentrations with the ability to promote the expression and production of insulin-like growth factor. The extract makes the product more amenable to use in preparations for use in conditions that are associated with reduced insulin-like growth factor levels in humans and animals, including growth, muscle mass, strength and repair, arthritis, bone formation and osteoporosis, dysmobility in the elderly, improved liver and gastrointestinal function, cachexia, fertility, fetal and neonatal growth restriction, aquaculture and animal farming.

14 Claims, 5 Drawing Sheets

METHODS AND COMPOSITIONS TO ENHANCE ENDOGENOUS IGF PRODUCTION AND THEIR USES

This application is a continuation of U.S. application Ser. No. 10/596,655, now abandoned, which was both: the National Stage application of International Application no. PCT/US04/43760, filed Dec. 22, 2004, which claims benefit of U.S. Provisional Application No. 60/531,266, filed Dec. 22, 2003; and also a continuation in part of application Ser. No. 10/676,459, filed on Sep. 30, 2003, now abandoned, which is a continuation in part of U.S. application Ser. No. 09/655,598 filed on Sep. 5, 2000, now abandoned, which claims benefit of U.S. provisional application No. 60/152,468, filed on Sep. 3, 1999.

BACKGROUND OF THE INVENTION

Field of Invention

Aging, compromised growth and certain disease states are associated with a decline in levels of insulin-like growth factor ("IGF"). This deficit leads to morbidity, compromised quality of life, growth restriction and increased risk for death. While growth hormone primarily regulates the hepatic production of IGF, options focused on elevating tissue production of IGF are not available.

By contrast, there are a wealth of approaches to reduce IGF production at these sites including hypoxia, aging, cytokines, matrix metalloproteases, infection and heightened immunity.

IGF is highly conserved and serves comparable roles in many species. It is a primary determinant of growth in the young, provides an anabolic effect and enhances muscle tone and strength, as well as maintains and promotes cartilage and bone health, quality and density. IGF functions to regulate the tissue uptake of glucose from whence its name is derived. It is also formed locally within the gonads and promotes fertility and fetal development. IGF promotes the resistance of tissues to stress, toxic and inflammatory challenges and promotes tissue repair.

The challenge to date has been how to promote or restore IGF production in states where IGF can provide a significant benefit. The oral administration of IGF is ineffectual as it is degraded by the digestive system. Similar problems exist with the oral administration of growth hormone and furthermore, it cannot stimulate local IGF production in many of the desired applications.

The Brassicaceae vegetable, Maca (*Lepidium* species) is eaten by indigenous people at high altitudes in the Andes. Researchers have discovered that the indigenous people do not suffer at the rate of hypoxia expected, which has been described to reduce IGF production—a critical determinant of fetal growth. Contrarily, Maca has been correlated with the restoration of fetal growth compromised by high altitude. Previous Maca researchers have characterized it as an aphrodisiac; however, Maca benefits cannot be explained by a stimulation of testosterone, estrogen, progesterone, prolactin, gonadotrophins or thyroid hormone. These classic sex steroid, gonatrophins, prolactin and thyroid hormone pathways are unaltered by maca or maca extracts and cannot adequately explain Maca's biological effects. The mechanisms for the purported therapeutic activities are elusive. Finally, Zheng et al (U.S. Pat. Nos. 6,267,995, 6,428,824, 6,552,206) disclose uses of aqueous, agueous:organic and preferably organic Maca extracts for deriving lipidic materials with applications for use in cancer and fertility but primarily sexual dysfunction (Urology, 55:598-602, 2000).

SUMMARY OF THE INVENTION

Aspects of the invention are summarized below to aid the understanding of the embodiment of the invention and the application. Yet, the invention is fully described by the claims of the application.

The disclosure herein defines the mechanism by which Maca provides benefits and forms the link to enhanced tissue production of IGF-1. Maca is demonstrably anabolic and growth promoting in farmed fish when Maca or Maca extracts are included in their diets. Additionally, Maca extracts, particularly polar extracts, directly stimulate IGF production as demonstrated using human chondrocytes obtained from surgical specimens of cartilage.

Given that suppressed IGF is a critical contributor to the complications and pathology of numerous disease states and the aging process, a new approach that enhances IGF levels provides a significant improvement in how these conditions are managed. The methods and compositions described herein concentrate the desired bioactive constituents with the ability to promote IGF and provide solutions to these conditions.

There is a general recognition that insulin-like growth factor (IGF) is an important determinant of growth in young animals. Its production declines with age and in so doing contributes to the symptoms of aging, such as decreased mobility, muscle wasting and strength, osteoporosis, osteoarthritis, diabetes and fertility. The suppression of IGF in these and disease states contributes to the pathology of those conditions. Nevertheless there are limited opportunities to restore or raise suppressed or inadequate IGF levels. Growth hormone is a well-known stimulus but primarily targets hepatic IGF formation with little influence on target tissue production of IGF. Growth hormone additionally and simultaneously stimulates the production of the inactivating IGF binding proteins that limit the bioactivity of IGF.

No pharmacological agents or substances are available to directly promote endogenous IGF production in target tissues independent of growth hormone. The present invention describes compositions, and methods of making the compositions from a natural source, that meets these unmet challenges and in so doing offers a significant innovation to the treatment of these various disorders.

Compositions described herein concentrate the bioactivity, derived from a natural source from the Family Brassicaceae, Maca, and demonstrates a significant and sustained elevation of IGF-1 gene expression in muscle. More particularly, the parent botanical and polar extracts, but not lipidic extracts, promote anabolism and growth in farmed trout as demonstrated by the results of a bioassay system that is critically dependent on IGF.

The present invention also describes methods that isolate and concentrate the polar, non-lipidic components of Maca that promote levels of IGF. In comparison, it offers a distinct advantage over the parent botanical and other extraction methods that concentrate lipidic components for other applications. Additionally, the invention teaches new methods and therapies for addressing states or complications associated with disease or aging.

DESCRIPTION OF EMBODIMENTS

Figure 1:
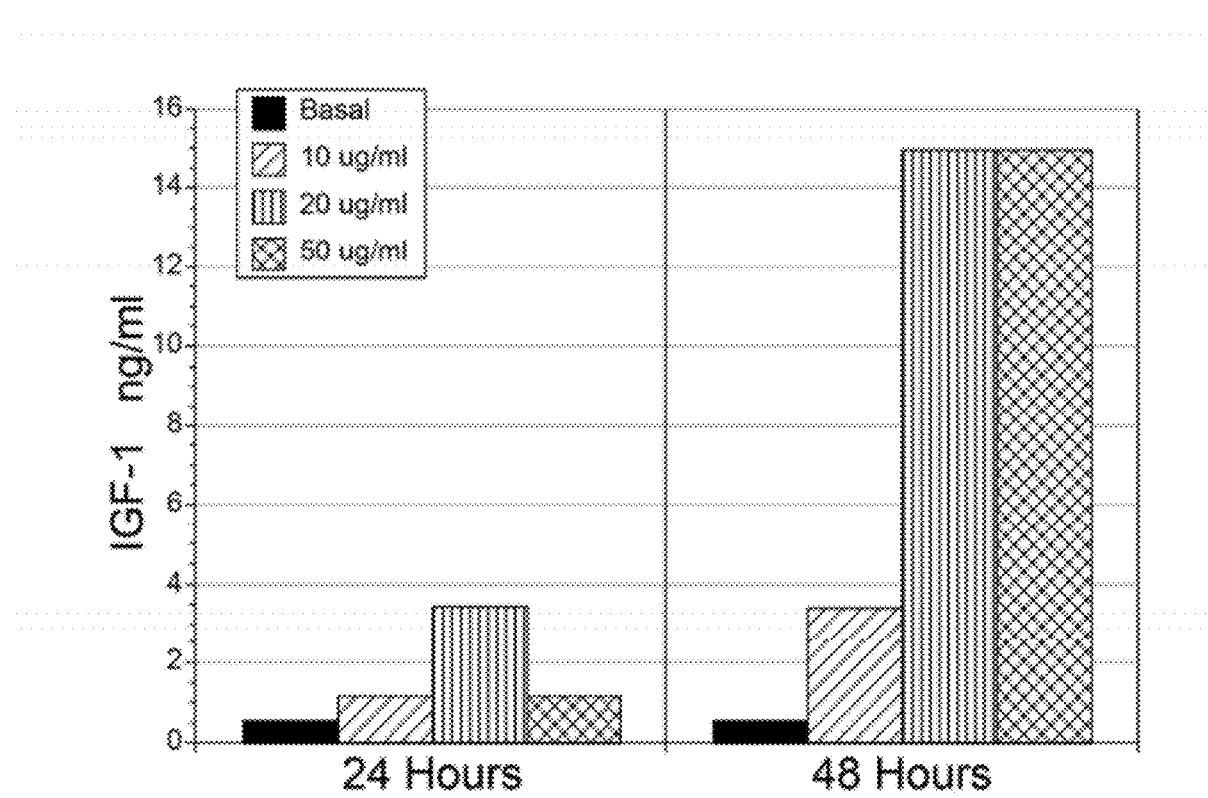
FIG. 1: Enhanced production of IGF-1 in human chondrocytes, obtained from surgical cartilage specimens, treated with the Maca extracts (SPI 249) at 10, 20 and 50 ug/ml measured at 24 and 48 hours in culture. IGF-1 levels in the media were determined by enzyme linked immunosorbent assay (ELISA). SPI 249, an aqueous extract, was effective in dramatically raising IGF-1 production in a sustained manner. Growth hormone was not present in these assay conditions.

According to one aspect of this invention, a process that concentrates polar components optimizes the extraction of *Lepidium* species ("Maca"), and the Brassicaceae family, to promote the expression of the gene for insulin-like growth factor (IGF) in a manner that is independent of growth hormone. This extraction process concentrates the parent material by at least 75%, independent of lipidic constituents. Preferred methods to accomplish the aforementioned *Lepidium* species extraction are described by the procedures below but it is contemplated that a skilled practitioner could device obvious variations of the procedures given the disclosure herein and the desired results.

Methods and compositions of the invention concentrate the polar constituents of plant material of family Brassicaceae. *Lepidium* is the preferred genus and the preferred plant material includes the hypocotyls or roots. The material is exposed to a liquid that is subsequently evaporated to resolve the polar components of the plant material. Preferred forms of liquid include gaseous forms including steam and/or water vapor. Preferred extraction methods also increase the surface area of the material exposed to the steam through mechanical manipulation (e.g. chopping, grinding, pureeing and macerating) to achieve a plant material in the form of pieces, granules, macerate, puree and/or powder.

An implementation of the process above comprises mechanically manipulated plant material spread upon mesh sheets or contained in mesh such that steam can pass through said material and said material exposed to steam in a controlled environment, such as a distillation vessel, for a period of between 15 minutes and eight hours. The steam exposed to the plant material is collected and condensed in a collector through temperature variation into a liquid and subsequently concentrated or depleted of the aqueous properties by process selected from the group consisting of evaporation, heating, vacuum drying, and lyophilization. The resulting extract of contains concentrated polar components and reduced lipid components, lignans and starches relative to the parent material.

Extraction Process 1

Maca hypocotyls are harvested, cleaned and washed to remove all detritus material and then the hypocotyls macerated. The macerate is then layered onto stainless steel mesh pans and aligned in a rack formation. Steam is then channeled through the mesh pans, the condensate collected and the macerate discarded. The steam is mixed with a low concentration of an alcohol. The condensate is reduced in volume by various means, including but not limited to evaporation under heat, vacuum or freeze drying. Heating to 75 degrees Celsius produced acceptable results. The resultant material concentrates polar components which stimulate IGF while depleting lipidic and complex starch components.

Extraction Process 2

Maca hypocotyls are harvested and cleansed to remove detritus material as described above. The hypocotyls are then dried and ground into a powder to increase the surface area of the material. This material is then placed on stainless steel mesh sheets, subjected to steam and the condensate collected. The condensate is reduced in volume by various means, including but not limited to evaporation under heat, vacuum or freeze drying. The resultant material concentrates polar components which stimulate IGF while depleting lipidic and complex starch components.

Enhanced IGF Expression, Production and Applications

The expression of insulin-like growth factor 1 (IGF-1) is a critical determinant of many conditions, where inadequate or decreased production is linked to dysfunction, disease and the symptoms of aging. Hepatic production of IGF can be stimulated by growth hormone but many tissues including skeletal muscle, cartilage, placenta and reproductive organs, produce IGF-1 for autocrine and paracrine reasons. Local production of IGF-1 in an autocrine manner has the advantage of not being affected by the co-production of inhibitory binding proteins that serve to sequester IGF-1 and limit its bioactivity. To date the development of agents that effectively augment this local production of IGF-1 has been elusive. On the other hand, aging as well as dietary alterations, hypoxia and disease can reduce local IGF-1 production.

Chondrocytes display endogenous IGF-1 production in order to promote anabolic functions like cartilage regeneration and repair. During inflammatory states like arthritis or acute injury, the chondrocytes produce and respond to mediators like interleukin-1, interleukin-6 and tumor necrosis factor to enter a catabolic state where cartilage is degraded and IGF production is reduced. This contributes to the loss of cartilage and joint structure and function in osteoarthritis. The human chondrocyte model mimics and is used to measure the deleterious effects of inflammation, infection and injury. A study was conducted using human chondrocytes obtained from surgical cartilage specimens. As illustrated by FIG. 1, cells were treated with aqueous Maca extracts (SPI 249) demonstrated a sustained up regulation of IGF-1 production that was dose-dependent as measured by ELISA. Chondrocyte IGF-1 production was significant at aqueous Maca extract doses approaching 10 ug/ml and greatest at doses of at least 20 ug/ml. IGF-1 production was apparent within 24 hours of a single exposure, with greatly enhanced levels observed at 48 hr. IGF-1 production was augmented with aqueous and aqueous/methanolic extracts of Maca.

Measurements of increased IGF-1 production over basal IGF-1 levels were measured at 24 and 48 hours. The data represented by FIG. 1 demonstrates an increase of IGF-1 levels at 24 hours. At 24 hours, a 10 ug/ml dose produced an IGF-1 increase of at least about 0.5 ng/ml (or a 100% increase) over the basal IGF-1 (0.5 ng/ml) level; a 20 ug/ml dose produced an IGF-1 increase of about 3 ng/ml (or a 600% increase); and a 50 ug/ml dose produced an increase of at least about 0.5 ng/ml (or a 100% increase). At 48 hours, a 10 ug/ml dose produced an IGF-1 increase of at least about 3 ng/ml (or a 600% increase) over the basal IGF-1 levels; and 20 and 50 ug/ml doses produced an IGF-1 increase of about 14.5 ng/ml (or a 2900% increase).

Figure 2:
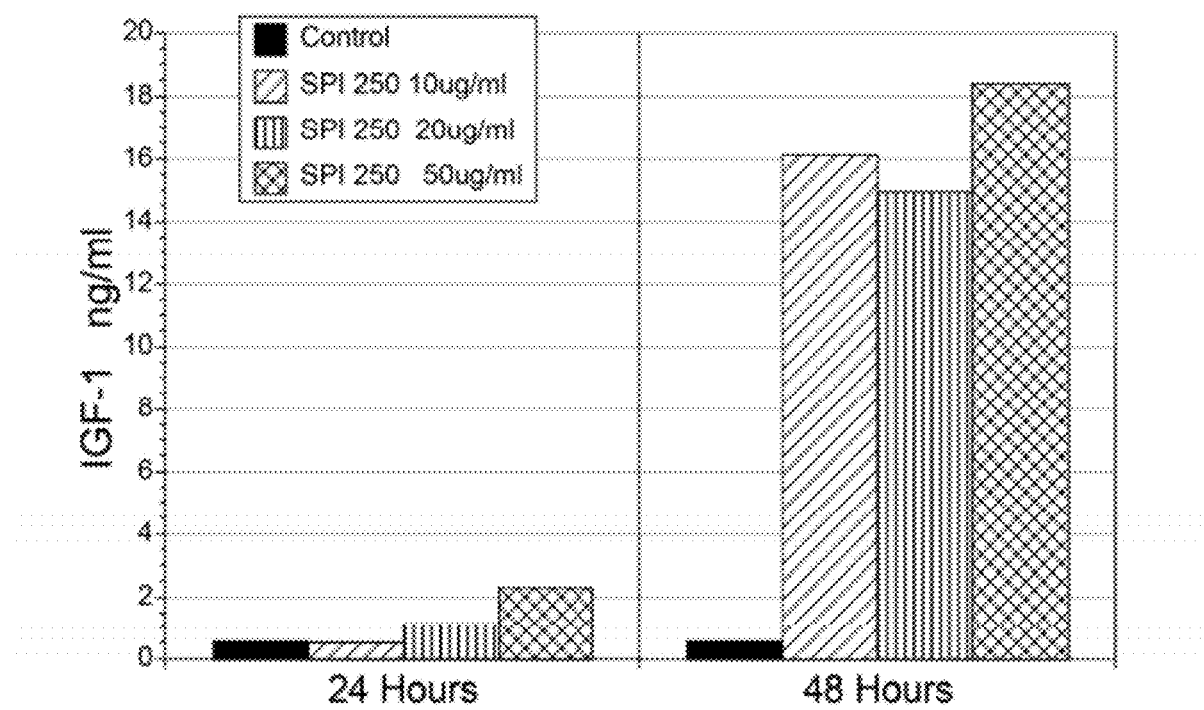
FIG. 2: Enhanced production of IGF-1 in human chondrocytes, obtained from surgical cartilage specimens, treated with the Maca extract (SPI 250) at 10, 20 and 50 ug/ml. IGF-1 production was quantified as media levels at 24 and 48 hours. As measured by ELISA. SPI 250, a methanol/aqueous extract, was effective in producing a sustained elevation of IGF-1 production. Growth hormone was not present in these assay conditions.
Figure 3:
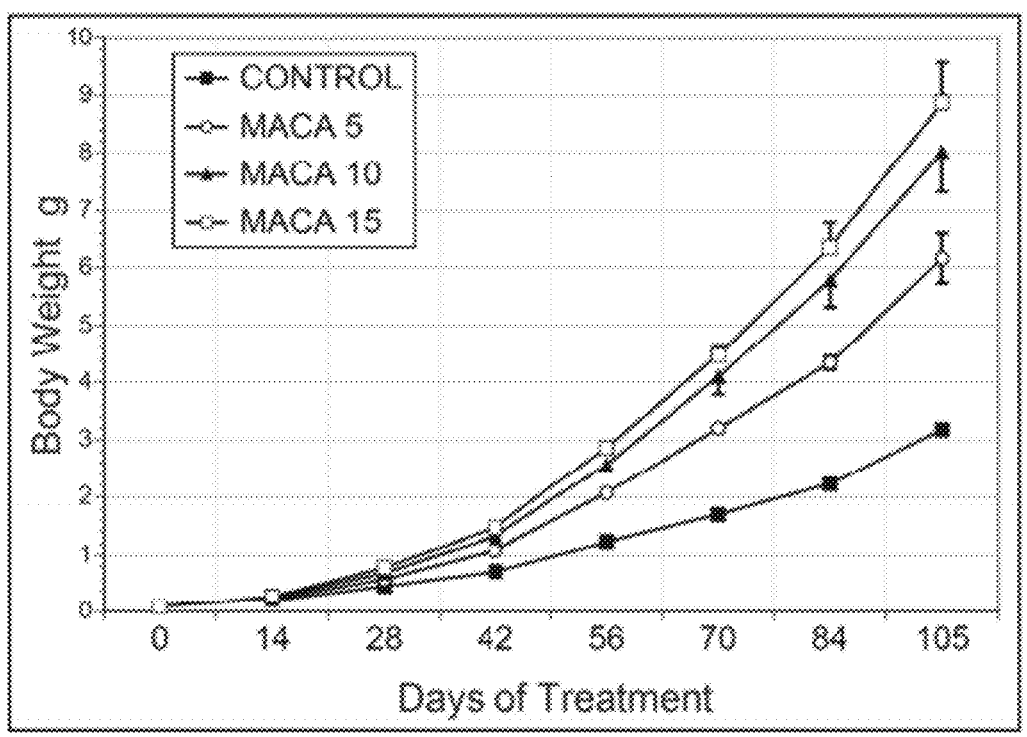
FIG. 3: Effects of Maca supplementation on the growth of Rainbow trout. Maca was administered in the feed at concentrations of 5, 10 and 15%, with growth trout size determined over a 14 week period.
Figure 4:
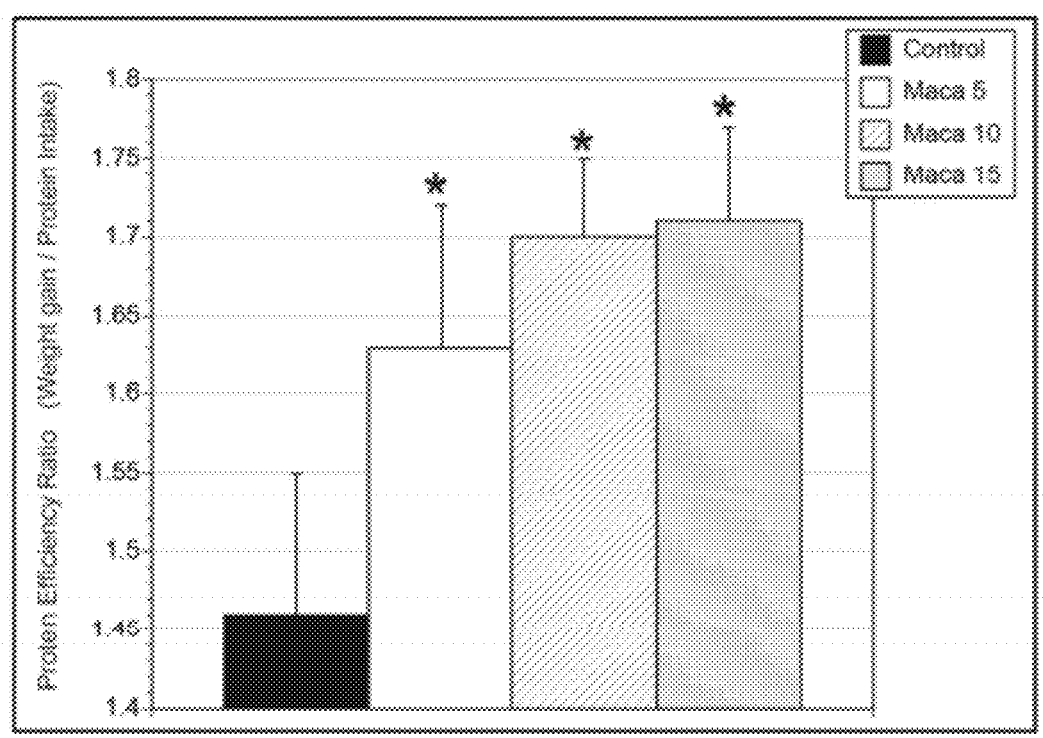
FIG. 4: The protein efficiency ratio, calculated from the body weight gain per unit of the protein intake, is significantly enhanced in all Maca fed trout groups (5, 10 and 15%). This is indicates a more efficient use of feed sources for growth purposes, or anabolism.
Figure 5:
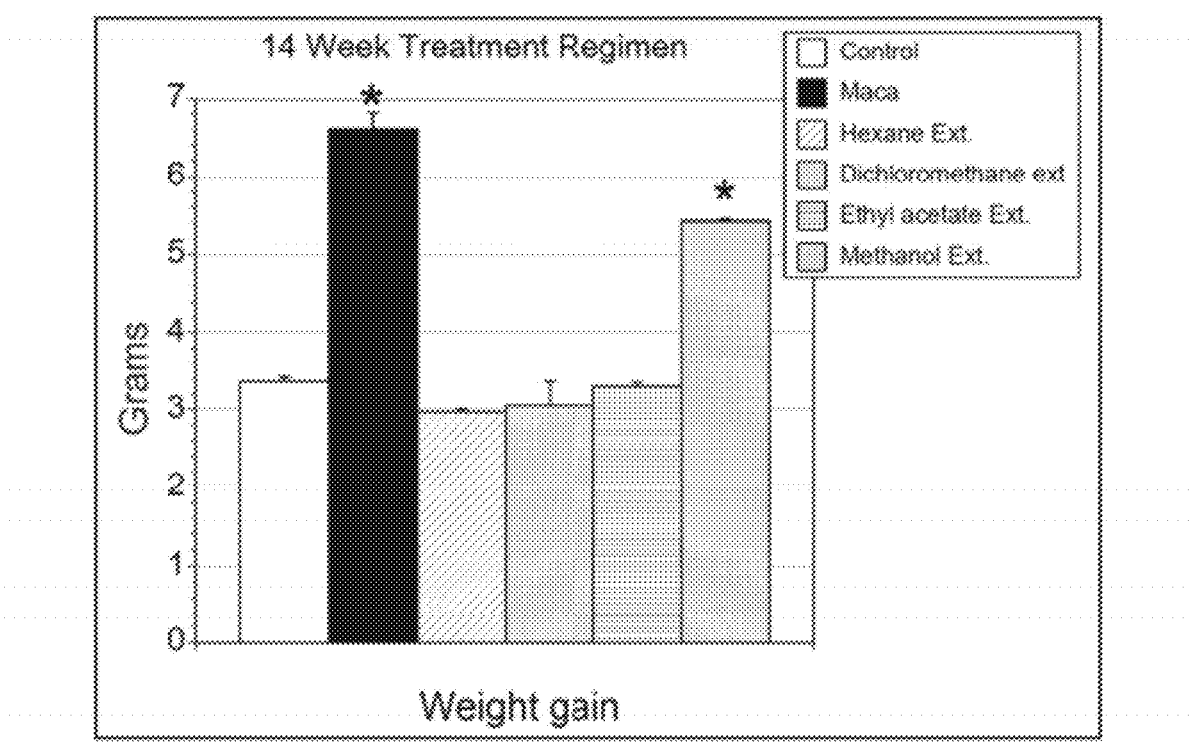
FIG. 5: Comparison of lipidic and methanolic extracts of Maca on trout growth. Only the Maca control and to a lesser extent the methanolic extract promoted fish growth. This indicates that the biological constituents responsible for growth are likely to be small, polar materials, and that extracts that are selective for these components would be the most effective.

As illustrated by FIG. 2, chondrocyte cells were treated with the aqueous/methanolic Maca extract (SPI 250) at 10, 20 and 50 ug/ml. IGF-1 production was quantified as media levels at 24 and 48 hours as measured by ELISA. The aqueous/methanolic extract, was effective in producing a sustained elevation of IGF-1 production. Chondrocyte IGF-1 production was significant at doses of at least 20 ug/ml and greatest at 50 ug/ml. This was apparent within 24 hours with a single exposure, with greatly enhanced levels observed at 48 hr. The ability of the Maca extracts (SPI 249 and 250) to promote IGF-1 gene expression suggests numerous applications or uses.

In fetal growth, Maca prevents altitude-associated fetal growth restriction. Hypoxia as experienced at high altitude is a direct suppressor of IGF-1 production and IGF-1 is a direct determinant of fetal growth. Compromised fetal growth caused by infection, elevated cytokine production or poor nutrition are also associated with compromised IGF production as it is a critical pathway for regulating fetal growth. Thus the elevation of endogenous IGF-1 would ameliorate associated conditions.

Fertility in both males and females is regulated by the local production of IGF-1. Given that ingestion of Maca can improve indices of fertility and prevent hypoxia-induced deficits in fertility, the enhanced IGF-1 promoting components of SPI 249 or SPI 250 extracts represent an innovative manner to stimulate IGF-1 dependent regulation of male and female fertility.

Cartilage is an example of a tissue source that produces IGF locally as an anabolic factor. IGF promotes cartilage growth, deposition of major matrix components and repair by preventing degradation induced by pro-inflammatory cytokines. As no therapy currently exists which directly promotes cartilage anabolism, IGF promoting methods and compositions contained in this embodiment represent an innovation in the therapy for conditions such as osteoarthritis.

As we age, there is a natural decline of IGF gene expression and production, which can be exacerbated by underlying inflammation. Those individuals with low IGF levels, such as the elderly, are at greater risk for restricted mobility, dysfunction and compromised quality of life. IGF not only promotes cartilage anabolism but also promotes strength, mass and tone of the surrounding skeletal muscle. This in turn provides greater strength and flexibility to the joint. Thus age-related declines in mobility, arthritis and quality of life can be treated with the composition SPI 249/250 described herein through its ability to promote endogenous IGF production, effectively reversing the decline associated with aging.

Increased muscle mass, strength and tone are anabolic characteristics of IGF-1 and thus SPI 249/250. As anabolic steroids have detrimental side-effects, SPI 249/2500 offers an alternative approach to enhance endogenous IGF-1 production as an anabolic stimulus devoid of the complications associated with pharmacological agents and thus confers a significant advantage.

In diabetes, glucose regulation is impaired by low insulin levels or depressed tissue responsiveness to insulin. By promoting the production of insulin-like growth factor (IGF) at the local (endogenous) level, SPI 249/250 improves glucose regulation and offers an alternative which could be beneficial in the treatment of diabetes.

SPI 249/250 through its actions on IGF-1 can promote weight loss and a leaner muscle mass by regulating glucose levels. To date weight management programs seeking to promote a leaner muscle mass have not been able to use approaches that enhance IGF-1 expression.

In young animals, humans, pigs, poultry, and ectotherms (i.e. fish), growth rate is determined by the production of IGF-1. Growth may be stunted by infection, inflammation, stress or diet which in turn suppresses the production of IGF-1. By enhancing IGF-1 production, SPI 249 and related extracts can promote growth. A study in fish farming where environmental influences have a large impact on growth and survival shows that Maca and polar but not lipidic extracts promote fish growth, anabolism and enhanced survival. A noted increase in the feed conversion ratio, where for each unit of food ingested, there was a corresponding 20% increase fish size, indicating anabolism.

Aging is associated with a reduction of IGF-1 expression and production, and this contributes to a reduced quality of life. Ingestion of Maca is known for its promotion of a feeling vitality that can be explained by enhanced IGF-1 production.

Cachexia or muscle wasting can occur in numerous conditions of infection, aging, altered immunity and is mediated at the tissue level by suppression of IGF production. By enhancing muscle production of IGF these deleterious effects can be negated.

Growth hormone is a stimulant for hepatic production of IGF-1 but is a poor regulator of tissue production of IGF-1. Individuals that are not responsive to growth hormone have depressed IGF-1 levels. SPI 249/250 by enhancing IGF-1 production at the tissue level independently of growth hormone offers a new approach to managing this condition.

Children suffering from persistent inflammation and cytokine production, as in inflammatory bowel disease or chronic renal inflammation, are growth impaired and display reduced levels of IGF-1, in part because of the ability of cytokines to suppress IGF-1 gene expression. By enhancing the endogenous production of IGF-1, SPI 249/250 acts as a novel means of treating these individuals and restoring growth rates.

Bone formation and healing is amplified by IGF-1. Young and the elderly are dependent on IGF-1 production for adequate bone density and quality. By increasing IGF-1 production, SPI 249/250 is an innovative treatment for osteoporosis, enhanced bone growth in childhood and to assist in fracture repair.

Low IGF-1 levels as seen in cirrhosis are associated with adverse outcomes and are considered pathogenic to the complications of cirrhosis. Resistance to the stimulatory effects of growth hormone is common. By providing an alternative approach to raising IGF levels, SPI 249/250 offers an innovative approach to managing cirrhosis and other conditions of hepatic damage such as toxic substance-induced damage and gastrointestinal disease.

Deficits in cognition associated with aging are associated with reduced IGF-1 levels. By elevating IGF-1 production, SPI 249/250 may pose a unique means of treating the cognitive problems of the elderly, including Alzheimer's disease.

Joint, muscle and tissue injury is associated with enhanced local pro-inflammatory mediators including matrix metalloproteases, which promote tissue degradative processes and diminished IGF-1 production. These can limit the repair process and complete healing. By stimulating the production of IGF-1, SPI 249/250 can promote repair and limit degradative processes to facilitate a more effective and rapid repair of injuries.

Pro-inflammatory cytokines, enzymes and processes promote catabolic events and suppress IGF-1 production. Thus, IGF-promoting SPI 249/250 in combination with antioxidants or redox based inhibitors of pro-inflammatory Considering the known effects of zinc, calcium and dietary proteins on bone and formation and strength, the combination of these agents with SPI 249/250 would be expected to produce a more effective treatment for disorders of musculoskeletal system.

As to a further discussion of the manner of usage and operation of the methods and compositions of present invention, the same should be apparent from the above description. Accordingly, no further discussion relating to the manner of usage and operation will be provided. With respect to the above description then, it is to be realized that the optimum variables for the disclosed methods or uses of the compositions of the invention, to include variations in time, size, materials, shape, form, function and manner of operation, and use, are deemed readily apparent and obvious to one skilled in the art, and all equivalent relationships to those illustrated in the figures and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention

What is claimed is:

1. A method of treating degradation of cartilage by increasing the production of Chondrocyte IGF-1 comprising administering at least about 10 ug per 0.5 ng of basal IGF-1 level of an extract of plant material selected from the group consisting of hypocotyls and roots from family Brassicaceae genus *Lepidium*, with concentrated polar components and reduced lipid and starch components and made by drying a condensate formed by a process of exposing said plant material to steam produced from at least one solvent including at least water and subsequent depletion of aqueous properties to concentrate the polar components by at least 75% over the unextracted plant material.

2. The method of claim 1 further comprising administering at least about 20 ug per 0.5 ng of basal IGF-1 level.

3. The method of claim 1 further comprising administering at least 50 ug per 0.5 ng of basal IGF-1 level.

4. The method of claim 2 further comprising administering a dose of between 20 ug and 50 ug per 0.5 ng of basal IGF-1 level.

5. The method in claim 1 wherein the Chondrocyte IGF-1 production is sustained for at least twenty four hours.

6. A method of producing an increase of at least 3 ng of Chondrocyte IGF-1 per 0.5 ng of basal IGF-1 level comprising administering per 0.5 ng of basal IGF-1 level, at least about 10 ug of a polar extract made by exposing plant material selected from the group consisting of hypocotyls and roots of family Brassicaceae genus *Lepidium* to steam produced from at least one solvent including at least water, and subsequent depletion of aqueous properties to concentrate the polar components by at least 75% over the unextracted plant material.

7. The method of claim 6 wherein the increase is sustained 24 hours.

8. The method of claim 6 wherein at least 50 ug of the polar extract is administered per 0.5 ng of basal IGF-1 level.

9. The method of claim 8 wherein the increase is sustained 24 hours.

10. A method of producing an increase in IGF-1 production in human cartilage cells for at least 24 hours comprising administering per 0.5 ng of basal IGF-1 level, at least 10 ug of polar extract made by exposing plant material selected from the group consisting of hypocotyls and roots of family Brassicaceae, genus *Lepidium* to steam produced from at least one solvent including at least water and subsequent depletion of aqueous properties to concentrate the polar components by at least 75% over the unextracted plant material.

11. The method of claim 10 wherein at least 20 ug of the polar extract per 0.5 ng of basal IGF-1 level is administered and the result is sustained 48 hours.

12. The method of claim 11 wherein the increase is at least 0.5 ng per 0.5 ng of the basal level of IGF-1.

13. The method of claim 10 wherein at least 50 ug of the polar extract is administered per 0.5 ng of basal IGF-1 level and the increase in IGF-1 is sustained 48 hours.

14. The method of claim 13 wherein the increase is at least 0.5 ng per 0.5 ng of the basal level of IGF-1.

* * * * *